(12) United States Patent
Steglich et al.

(10) Patent No.: US 11,092,742 B2
(45) Date of Patent: Aug. 17, 2021

(54) PHOTONIC SENSOR CHIP, PACKAGED PHOTONIC SENSOR DEVICE AND ARRANGEMENT

(71) Applicant: IHP GmbH—Innovations for High Performance Microelectronics/Leibniz-Institut fur Innovative, Frankfurt an der Oder (DE)

(72) Inventors: Patrick Steglich, Frankfurt an der Oder (DE); Andreas Mai, Frankfurt an der Oder (DE); Christian Mai, Frankfurt an der Oder (DE)

(73) Assignee: IHP GMBH—INNOVATIONS FOR HIGH PERFORMANCE MICROELECTRONICS/LEIBNIZ-INSTITUT FÜR INNOVATIVE MIKROELEKTRONIK

( * ) Notice: Subject to any disclaimer, the term of this patent is extended or adjusted under 35 U.S.C. 154(b) by 0 days.

(21) Appl. No.: 16/718,595

(22) Filed: Dec. 18, 2019

(65) Prior Publication Data

US 2020/0200972 A1    Jun. 25, 2020

(30) Foreign Application Priority Data

Dec. 21, 2018  (EP) ..................................... 18215524
Apr. 1, 2019   (EP) ..................................... 19166562

(51) Int. Cl.
*G01N 21/77*    (2006.01)
*G01N 21/552*   (2014.01)
(Continued)

(52) U.S. Cl.
CPC ......... *G02B 6/1225* (2013.01); *G01N 21/553* (2013.01); *G01N 21/7703* (2013.01);
(Continued)

(58) Field of Classification Search
CPC ..................... G01N 21/7703; G01N 21/553
See application file for complete search history.

(56) References Cited

U.S. PATENT DOCUMENTS 9,417,186 B2 *   8/2016  Jakoby ................. G01N 21/552
10,451,543 B2 * 10/2019  Mueller ............. G01N 29/2418
(Continued)

FOREIGN PATENT DOCUMENTS

CN      107209107 A  *  9/2017  ........ B01L 3/502715
EP      1918693 A1      5/2008
(Continued)

OTHER PUBLICATIONS

Extended EP Search Report issued by the EPO dated Apr. 23, 2020 from EP Patent Application No. 19218716.9 17 pages.
(Continued)

*Primary Examiner* — Charlie Y Peng
(74) *Attorney, Agent, or Firm* — Ware, Fressola, Maguire & Barber LLP

(57) ABSTRACT

The invention relates to a photonic sensor chip comprising a semiconductor substrate with a cavity extending from a back side through an entire depth of the semiconductor substrate, a photonic plane located on the front side of the semiconductor substrate. The chip includes a photonic particle sensor element with an active-surface element having an exposed active surface facing towards the back side of the semiconductor substrate, for capturing selected particles from at least one fluid or gas to which the active surface is exposable. The cavity provides access to the active surface from the back side. The photonic particle sensor element receives an optical input wave via the photonic plane, to expose captured particles on the active-surface element to interaction with the optical input wave and to provide a resulting optical output wave having a spectral component
(Continued)

indicative of the interaction between the optical input wave and captured particles.

14 Claims, 12 Drawing Sheets

(51) Int. Cl.
　　*G02B 6/122*　　　(2006.01)
　　*G01N 31/22*　　　(2006.01)
　　*G02B 6/12*　　　(2006.01)

(52) U.S. Cl.
　　CPC ....... *G01N 31/223* (2013.01); *G02B 6/12021* (2013.01); *G02B 2006/12133* (2013.01)

(56) References Cited

U.S. PATENT DOCUMENTS

| | | | |
|---|---|---|---|
| 10,502,620 B1 * | 12/2019 | Meng | ........................ G01J 3/18 |
| 2005/0035278 A1 | 2/2005 | Margalit et al. | |
| 2009/0087137 A1 | 4/2009 | Doan | |
| 2014/0263948 A1 * | 9/2014 | Lee | .................... G01N 21/7746 250/206 |
| 2018/0159293 A1 | 6/2018 | Bovington et al. | |
| 2019/0056303 A1 * | 2/2019 | Bahl | .................. G01N 15/1459 |

FOREIGN PATENT DOCUMENTS

| | | | | |
|---|---|---|---|---|
| EP | 2515099 A1 | 10/2012 | | |
| EP | 2581730 A1 | 4/2013 | | |
| KR | 20120016297 A | * | 2/2012 | ............. G01N 21/05 |
| WO | WO-2009060357 A1 | * | 5/2009 | .......... B01L 3/50273 |
| WO | 2018/150205 A1 | | 8/2018 | |

OTHER PUBLICATIONS

European Search Report issued by the EPO dated Oct. 25, 2019 from EP Patent Application No. 19166562.9, 15 pages.

* cited by examiner

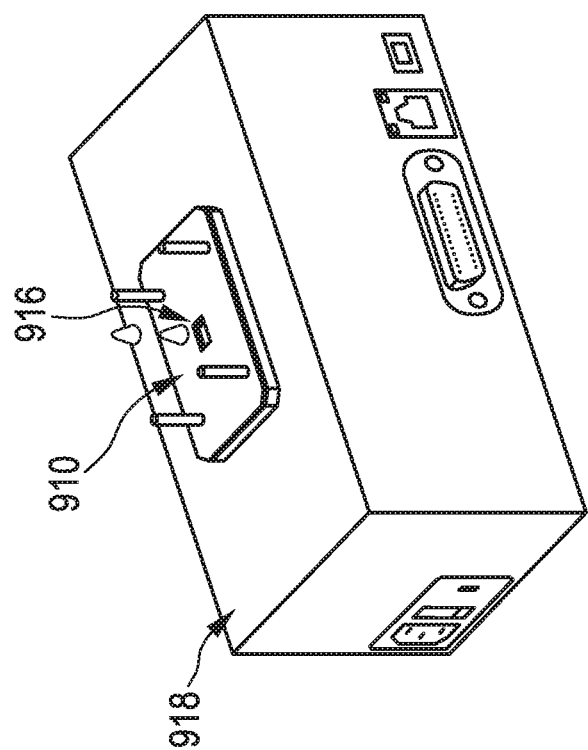
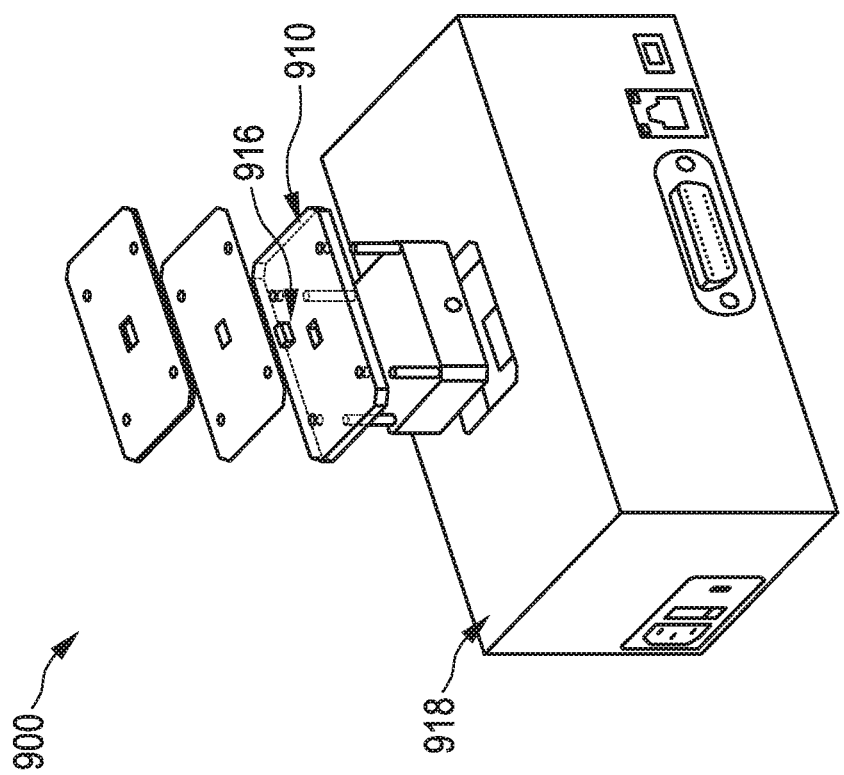
FIG. 9

PHOTONIC SENSOR CHIP, PACKAGED PHOTONIC SENSOR DEVICE AND ARRANGEMENT

CROSS REFERENCE TO RELATED APPLICATIONS

This application claims priority under 35 USC § 119 to European Patent Application No. 18215524.2 filed on Dec. 21, 2018 and European Patent Application No. 19166562.9 filed on Apr. 1, 2019, which applications are hereby incorporated by reference in their entirety.

TECHNICAL FIELD

The present invention relates to a photonic sensor chip, to a packaged photonic sensor device and to a photonic sensor arrangement.

BACKGROUND OF THE INVENTION

Photonic sensors have contributed to major advances in food diagnostics, environmental monitoring, veterinary diagnostics and medical technology through rapid and accurate analysis of a wide range of particles in a fluid or a gas. In fact, great progress has been made in recent years in photonic sensor technology for bioanalytics. Surface plasmon resonance (SPR) has become a standard technology applied for this purpose. However, as of today, this technology is quite expensive in terms of equipment and total costs regarding chips and service, and known sensors based on SPR are rather bulky.

SUMMARY OF THE INVENTION

It would thus be desirable to achieve cheaper photonic sensor devices that are suitable for detecting particles in bioanalytics and offer the prospect of cost-effective on-site analysis.

According to the first aspect of the invention, a photonic sensor chip comprises:
 a semiconductor substrate having a front side and a back side;
 at least one cavity extending from the back side through an entire depth of the semiconductor substrate;
 a photonic plane located on the front side of the semiconductor substrate and including
  at least one photonic particle sensor element with an active-surface element having an exposed active surface facing towards the back side of the semiconductor substrate and configured for capturing selected particles from at least one fluid or gas to which the active surface is exposable, wherein the least one cavity provides access to the active surface from the back side of the semiconductor substrate; and wherein
  the photonic particle sensor element is configured to receive an optical input wave via the photonic plane, to expose particles captured by the active-surface element to interact with the optical input wave and to provide a resulting optical output wave having a spectral component indicative of the interaction between the optical input wave and the captured particles.

The photonic sensor chip includes at least one cavity extending from the back side through an entire depth of the semiconductor substrate. The cavity provides access to the active surface of the photonic particle sensor element from the back side of the semiconductor substrate. Thus, despite the arrangement of the photonic particle sensor element on the front side of the semiconductor substrate, it has an active-surface element for capturing particles that is exposed for access from the back side of the semiconductor substrate. Non-limiting examples of particles to be detected by the photonic particle sensor include, depending on a particular application purpose of a given embodiment, toxins, bacteria, viruses, allergens, antibiotics, hormones and other particles such as molecules.

The photonic sensor chip allows, by means of its structure, fabricating the photonic particle sensor element independent from the constraints of device structure fabrication on the front side of the semiconductor substrate. In particular, the active surface of the active-surface element facing towards the back side of the semiconductor substrate and configured for capturing selected particles can be fabricated after fabrication of any front side structures. Also, fabrication steps required for forming the active-surface element can be performed separately from fabrication processes for manufacturing the photonic plane on the front side of the semiconductor substrate. This allows using materials in the fabrication of the active-surface element that are not compatible with standard front-end-of-line (FEOL) technology such as NMOS, PMOS, CMOS or BiCMOS, whereas the photonic plane on the front side of the semiconductor substrate can be fabricated using such highly developed and cost-efficient FEOL technology.

Furthermore, the structure of the photonic sensor chip makes sure that, in operation, a fluid or gas which transports particles to be detected will not get in contact with the front side of the semiconductor substrate. Thus, potential exposure of the photonic sensor chip to a fluid or gas or to chemical reactions is restricted to the back side of the semiconductor substrate. This allows including integrated microelectronic components and complete electronic circuits on the front side of the photonic sensor chip, which will be described further below in more detail in the context of preferred embodiments. Therefore, the proposed photonic sensor chip is advantageously suited for integration in known semiconductor photonics concepts, including for instance complex device structures with integrated photonic, electro-optical, optoelectronic and electronic components on different levels.

The photonic particle sensor element comprises a waveguide arranged in the photonic plane for guiding the optical input wave to the active-surface element and for guiding the resulting optical output wave from the active-surface element to a light detector of the photonic particle sensor element. Thus, improving the light guiding to the active-surface element is achieved. The waveguide guides the optical input wave in a defined manner to the active-surface element, and guides the resulting optical output wave to a light detector of the photonic particle sensor element.

The photonic sensor chip further comprises an electrically drivable phase shifter element. The phase shifter element is configured to set and maintain a predetermined phase shift to be effected by the active-surface element alone, i.e., without influence by particles to be detected. With the phase shifter element, the photonic sensor chip is able to adapt the phase shift in order to improve the desired signal, i.e. desired information provided by the active-surface element with the optical output wave. As a result, a signal-to-noise ratio of the optical output wave can be increased to improve the detectability of interaction between the optical input wave and the particles captured by the active-surface element.

In the following, embodiments of the photonic sensor chip will be described.

In some embodiments, the photonic sensor chip further comprises a control unit. The control unit receives the output signal of the light detector and is configured to drive the operation of the photonic particle sensor element on the photonic sensor chip. In particular, the control unit is configured to drive operation of the phase shifter element in dependence on the received output signal, in order to set and maintain a predetermined phase shift effected by the active-surface element alone. In such embodiments, the light detector receives a signal indicative of a phase shift with respect to a stabilized reference phase. Thus, a stabilized intensity is achieved, and an intensity change is reliably attributable to a useful signal.

In preferred embodiments, the photonic particle sensor element includes a photonic resonator, or interferometer structure, preferably in integrated form within the photonic sensor chip. The photonic particle sensor element is configured to exhibit a change of a resonance condition of the photonic resonator or interferomenter structure, for instance in the form of a change of an optical resonance wavelength, in dependence on a type of particle captured. The light amount at the output of the photonic resonator or interferometer structure and detected by the light detector thus depends on the phase shift effected in presence of the captured particles and exhibits a resonance peak or resonance dip. The change of the resonance condition thus forms a "finger print" of a given type of captured particle. Thus, determining a change of the resonance condition before and after capturing of particles allows determining the type of captured particle.

In one embodiment, the resonance condition of the photonic particle sensor element can be changed by the phase shifter element as a result of the operation of the control unit. A control of the resonance condition is achieved in that the optical resonance of the photonic particle sensor element can be shifted. Such resonance control allows using a cost-effective monochromatic light source. Further, fabrication tolerances can change the resonance conditions that can be compensated by the phase shifter.

Suitably, to achieve sensitivity of the photonic resonator to a phase shift of any sign, the control unit is configured to control a shift of the optical resonance of the photonic particle sensor element such that the optical input wave received by the photonic particle sensor element lies on a resonance flank in absence of any captured particle. Captured particles thus cause either an increase or decrease of the light amount detected by the light detector, in dependence on a positive or negative phase shift effected by the particles. In another example, the resonance peak is used as the reference phase in absence of captured particles. In this alternative, captured particles always cause the same sign or direction of change of the light amount, irrespective of the sign of the phase shift effected by the captured particles.

Suitable electrically drivable phase shifter elements are an electrically drivable heating element embedded in the electrical interconnect stack, or an electrically drivable doped waveguide. The heating element or the doped waveguide is suitably connected via the electrical interconnects. The heating element is preferably a resistance heater formed in the first metal layer of the interconnect stack in a lateral region coinciding or overlapping with that of the waveguide. The heating element changes the resonance condition of the photonic particle sensor element via the thermo-optical effect. In preferred embodiments, the control unit receives a feedback signal from the light detector. This is particularly useful in embodiments providing resonance control. Here, the feedback signal can be used in a tuning process for tuning the phase shift effected by the phase shifter element in controlling the resonance condition of the optical resonance of the photonic particle sensor element to a desired spectral position.

In the latter example, the waveguide is doped in pn- or pin-diode configuration. The doped waveguide shifts the resonant condition of the photonic particle sensor element via changes in charge carrier density.

In a further embodiment, the phase shifter element comprises both, a heating element and a doped waveguide.

In an alternative embodiment, the heating element is used, beside resonance calibration, for optimum adjustment of temperature during the measuring process, in particular where a binding affinity of biomolecules is temperature dependent.

In a preferred embodiment the photonic sensor chip further comprises a data acquisition unit configured to sample an output signal of the light detector. The photonic sensor chip of this embodiment is advantageous due to its compact design.

In such embodiments, an electrical interconnect stack is preferably arranged on top of the photonic plane and comprises electrical interconnects for conducting electrical operating power and to conduct electronic signals to and from the control unit and the data acquisition unit. The electrical interconnect stack typically comprises the electrical interconnects on different metal planes which are separated from each other by a respective dielectric material layer and conductive vias, for conducting electrical operating power, and for conducting electronic signals to and from the control unit and the data acquisition unit.

Such lab-on-a-chip design allows fabrication of particularly small and cost-effective solutions suitable for flexible application of the photonic sensor chip, e.g., in on-site diagnostics, for instance in dairy farming or mobile blood diagnostic equipment.

As indicated before, the inventive photonic sensor chip increases the flexibility of usage. In further preferred embodiments of the photonic sensor chip, a microfluidic substrate is connected to the back side of the semiconductor substrate and comprises at least one microfluidic channel connecting an inlet for the fluid and an outlet for the fluid with the cavity. Regarding fabrication complexity, the connection of the microfluidic substrate on the back side of the semiconductor substrate according to the present embodiment is simpler in comparison to providing the microfluidics on the front side of the semiconductor substrate for access to the photonic particle sensor element.

In different embodiments of the photonic sensor chip of this kind, the microfluidic substrate is made of a plastic, glass, quartz or a semiconductor, enabling an application-specific material selection for the microfluidic substrate. The connection of the microfluidic substrate to the semiconductor substrate can be realized by wafer bonding for many of the materials mentioned. Wafer bonding is a well-known and reliable technique. The ability to use a wafer bonding technique thus forms an additional advantage of the of the structure of the photonic sensor chip which substantially simplifies the fabrication process.

Preferably, the semiconductor substrate is a silicon substrate, which for instance is formed from an industry-standard silicon wafer. In some embodiments of the photonic sensor chip of this kind, the waveguide in the photonic plane is arranged on a local island-like silicon-on-insulator (SOI) structure that is embedded in the bulk of the silicon substrate. This allows flexibly combining the advantages of using an SOI substrate for the photonic components and of using a silicon substrate surface for the microelectronic components and electrical connection lines.

In preferred embodiments of the photonic sensor chip, the active-surface element comprises a waveguide section of the waveguide. The waveguide section comprises at least one functionalized surface section configured for capturing the selected particles by selective interaction, and has an optical path length that depends on an amount of particles captured by the active surface. The waveguide section, in some of these embodiments, has a ring resonator geometry. In alternative embodiments, the waveguide section is a ring assisted Mach-Zehnder interferometer or a Fabry-Perot resonator with photonic crystals. All of these waveguide sections have the similarity that they provide an optical signal conveying the information on detected particles in a manner that is suitable for converting into an electrical signal by the light detector.

In other embodiments of the photonic sensor chip, the photonic particle sensor element comprises a plurality of active-surface elements optically arranged in a series connection and upstream of the light detector. Such arrangement of active-surface elements optically arranged in a series connection allows to increase the signal-to-noise ratio of the resulting optical output wave to be transformed into a corresponding electrical signal by the light detector.

Different waveguide types can be used in the photonic sensor chip. In different exemplary embodiments, the waveguide is a strip waveguide, a slot waveguide, a rib waveguide or a strip-loaded slot waveguide on top of an insulating material layer.

In another embodiment, the photonic sensor chip comprises a plurality of photonic particle sensor element arranged in parallel. Thus, a plurality of active-surface elements (or respective series of identical active-surface elements) are provided upstream of a corresponding plurality of light detectors. Such a parallel arrangements of photonic particle sensor elements enables the detection of different selected particles in parallel.

Regarding the functionalized surface section of the waveguide section, different functionalization methods are possible. In some embodiments of the photonic sensor chip, the functionalized surface section is functionalized chemically. In exemplary embodiments of this kind, specific antibodies or ligands are covalently bonded to the surface of the waveguide section that forms the active surface element, resulting in a functionalized surface section. In other embodiments of the photonic sensor chip, the functionalized surface section is functionalized physically. For instance, the surface of the waveguide section forming the active-surface element has a roughness suitable for capturing particles. The roughness can be established in the fabrication process by physical treatment of the active-surface element, e.g., by ion bombardment.

In other embodiments, a highly reflective metal, e.g. gold, is arranged between the functionalized surface section of the active-surface element and the waveguide section as an intermediate layer. This layer stack is suitable for application in a surface plasmon resonance spectroscopy technique. It is a further advantage of the photonic sensor chip of the present invention that such intermediate layer of gold can be deployed, even if industry standard fabrication processes are used for front side fabrication. Gold is a material that must not be used in standard FEOL processing.

In different embodiments of the photonic sensor chip, the waveguide is substantially made of silicon, silicon nitride, silicon oxynitride or germanium. In the case of using silicon for the waveguide, either crystalline silicon, polysilicon or amorphous silicon can be used, depending on the requirements of the given application case.

In a preferred embodiment, the photonic sensor chip comprises at least one light source, e.g., a vertical-cavity surface-emitting laser source or a light-emitting diode, connected to the waveguide and configured to generate and emit the optical input wave. The light source is arranged in the photonic plane. Alternatively, the light source is arranged in the interconnect stack or on top of the interconnect stack. In some variants of this embodiment, the light source is attached to the photonic sensor chip by a bonding technique, for example, via die-to wafer or wafer-to-wafer bonding.

According to a second aspect of the invention, a packaged photonic sensor device is provided. The packaged photonic sensor device comprises:

- a photonic sensor chip according to an embodiment of the first aspect of the invention, wherein the photonic particle sensor element comprises a waveguide arranged in the photonic plane for guiding the optical input wave to the active-surface element and for guiding the resulting optical output wave from the active-surface element to a light detector of the photonic particle sensor element
- an electronic control chip electrically connected to the photonic sensor chip arranged on the carrier and comprising a control unit, which is configured to drive operation of the at least one photonic particle sensor element on the photonic sensor chip and a data acquisition unit configured to sample an output signal of the light detector;
- a package enclosing the photonic sensor chip and the electronic control chip and having an opening to ambient atmosphere facing the back side of the semiconductor substrate of the photonic sensor chip for providing access to the exposed active surface of the at least one photonic particle sensor element for the at least one fluid.

The photonic sensor chip can be arranged on a carrier and packaged by state of the art solutions, including a hole for providing access to the active-surface element of the particle sensor element of the photonic sensor chip.

According to a third aspect of the invention, a photonic sensor arrangement is provided. The photonic sensor arrangement comprises:

- a packaged photonic sensor device according to the second aspect of the invention or one of its embodiments, and
- a light source for generating the optical input wave, and an optical coupling element for coupling the optical input wave into the photonic plane of the photonic sensor chip.

The optical input wave is coupled into the photonic plane of the photonic sensor chip, for instance, by an optical fiber. Alternatively, the optical input wave is coupled into the photonic plane of the photonic sensor chip by a free-steel optic using a suitable lens. The package of the photonic sensor device must take the respective coupling of light into account.

In preferred embodiments the photonic sensor arrangement further comprises on the printed circuit board

- a data transmission unit configured to receive the output signal from the data acquisition unit and to transmit the output signal to an external device; and an interface unit configured to receive the output signal from the data acquisition unit and to indicate an amount of particles captured by the active surface.

This embodiment allows an immediate verification of the analysed particles. For example, a cross-check of allergens or germ content in food. Thus, such photonic sensor arrangement is used for quality assurance in food industry. Alternatively, such photonic sensor arrangement is used in medicine diagnostic, e.g. for analysing blood composition. Also, in some embodiments the presence of toxins in ambient atmosphere can be detected.

BRIEF DESCRIPTION OF THE DRAWINGS

In the following, further embodiments will be described with reference to the enclosed drawings. In the drawings:

FIG. 9 shows an embodiment of a photonic sensor arrangement;

DETAILED DESCRIPTION

Figure 1:
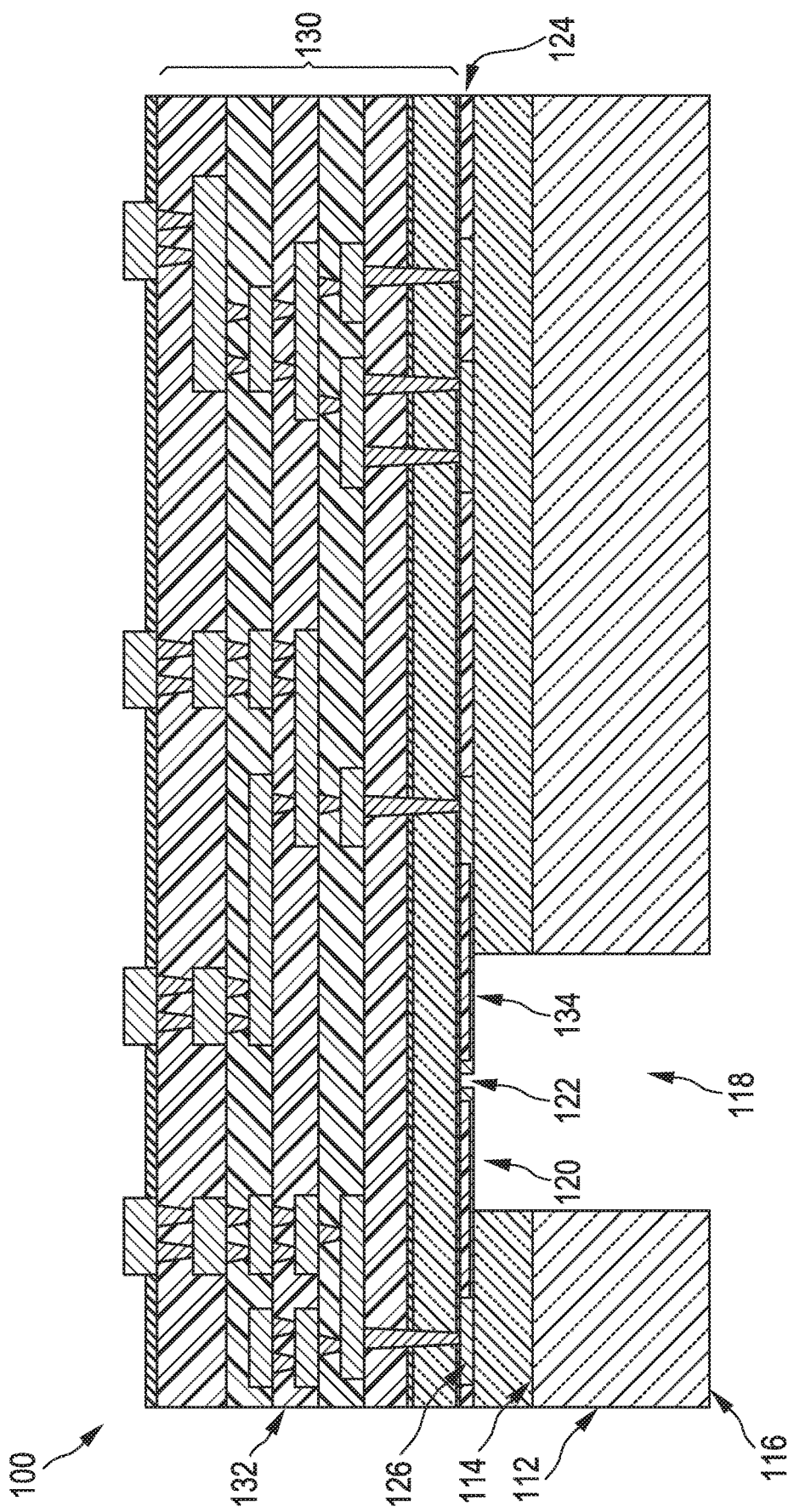
FIG. 1 shows a schematic cross-sectional view of an embodiment of a photonic sensor chip.

FIG. 1 shows a schematic cross-sectional view of an embodiment of a photonic sensor chip 100. The photonic sensor chip 100 comprises a semiconductor substrate 112 having a front side 114 and a back side 116. The photonic sensor chip 100 includes a cavity 118 extending from the back side 116 through an entire depth of the semiconductor substrate 112, which is for example a silicon substrate. The cavity 118 provides access to the active surface of the photonic particle sensor element 120 from the back side 116 of the semiconductor substrate 112. A photonic particle sensor element 120 is arranged on the front side 114 of the semiconductor substrate in a photonic plane 124. The photonic particle sensor element 120 comprises an active-surface element 122 for capturing particles that is exposed for access from the back side 116 of the semiconductor substrate 100. In this embodiment the active-surface element 122 comprises a waveguide section 134 of a waveguide, which waveguide serves for guiding an optical input wave in a defined manner to the active-surface element 122, and further for guiding a resulting optical output wave to a light detector (not shown here), which is in this example a photodiode, of the photonic particle sensor element. Advantageously, the waveguide is embedded in oxide layers.

On the front side 114 of the semiconductor substrate 112 of the photonic sensor chip 100, electro-optical and electronic components 126 are arranged, and an electrical interconnect stack 130 is provided on top of the photonic plane 124. The electrical interconnect stack 130 comprises electrical interconnects 132 for conducting electrical operating power to the electro-optical and electronic components, including the light detector, and to conduct electronic signals to and from the electro-optical and electronic components to their respective destinations on chip or to an interface to external circuits. The opto-electronic and electronic components are fabricated using known front-end-of-line (FEOL) such as NMOS, PMOS, CMOS or BiCMOS, or a photodiode as light detector and the interconnect stack 132 can be fabricated using standard back-end-of-line (BEOL) technologies. The electronic components 126 can for instance form a circuit section or a complete circuit of a control unit, a data acquisition unit or other electrical circuitry.

The shown photonic sensor chip 100 makes sure that, in operation, a fluid or gas which transports particles to be detected at the active-surface element 122 in the cavity 118 will not get in contact with the front side 114 of the semiconductor substrate 112. In this example, the measuring solution is applied directly to the sensor surface as a drop. Thus, potential exposure of the photonic sensor chip 100 to a fluid or gas or to chemical reactions is restricted to the back side 116 of the semiconductor substrate 112.

The combination of photonic components with state-of-the-art silicon-based microtechnology is forms key to development of a biosensors according to embodiments of the present invention.

Thus, while prior art photonic devices are etched from the wafer surface and subsequently functionalized and electronic circuits located on the individual metal levels cannot be integrated, the innovative approach exemplified by the embodiment of FIG. 1 uncovers the back of the photonic components. This approach enables for the first time an interaction between the analyte and the functionalized silicon waveguide and the simultaneous integration of electronic circuits on the chip top including the complete BEOL metallization layers.

Figure 2:
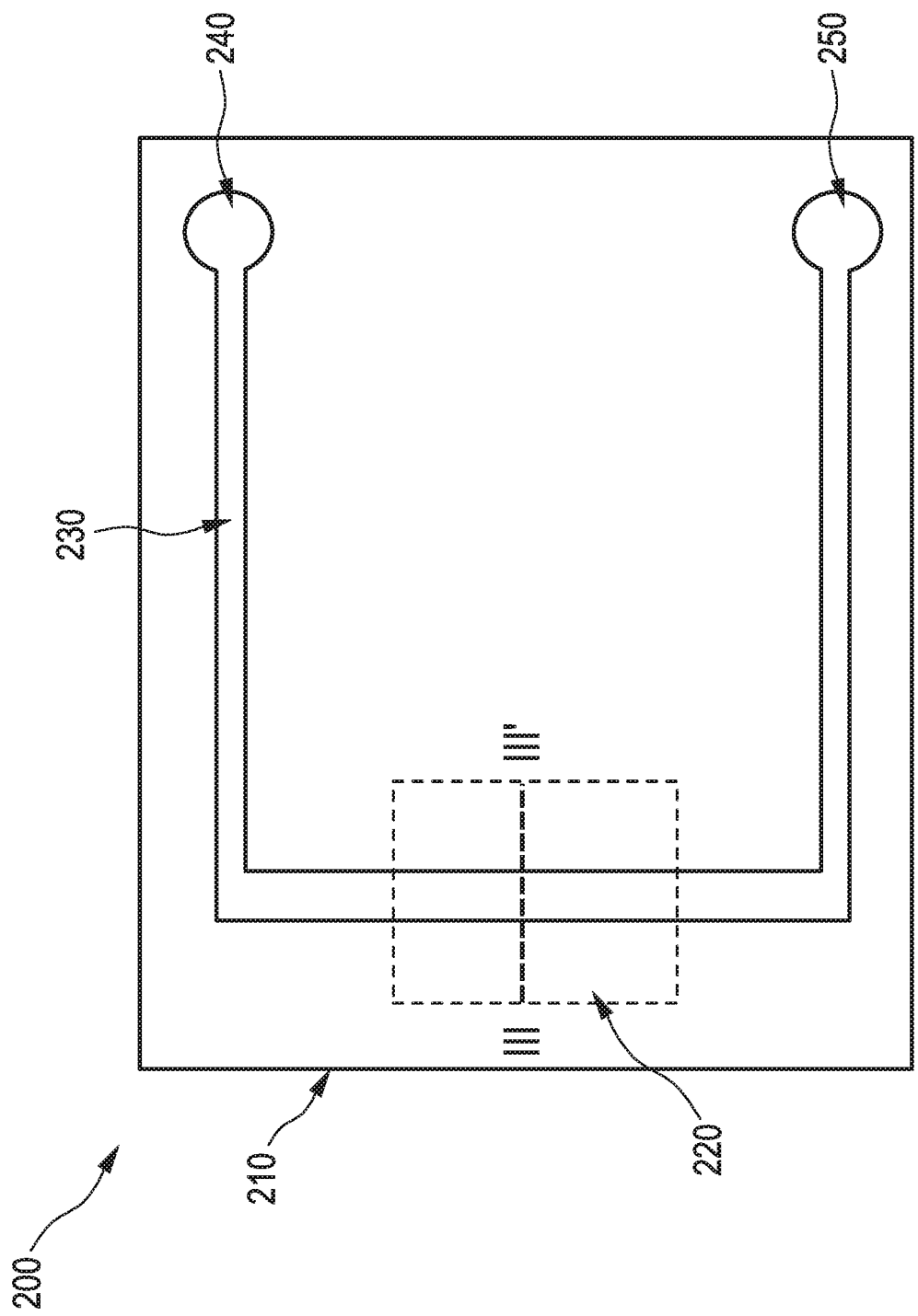
FIG. 2 shows a schematic backside view of a photonic sensor chip that includes a microfluidic substrate.
Figure 3:
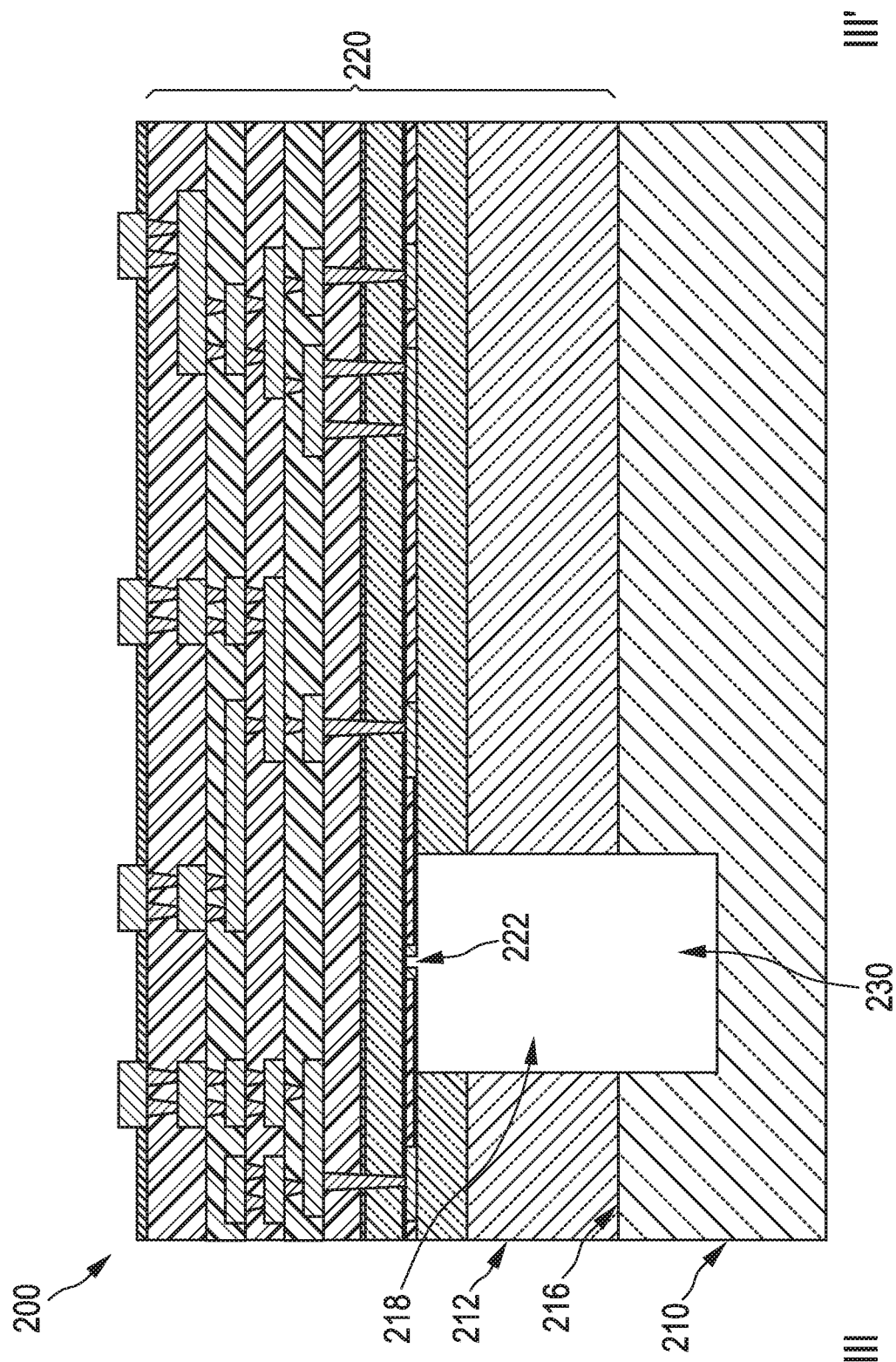
FIG. 3 shows a schematic cross-sectional view of the photonic sensor chip of FIG. 2 along a line III-III' shown in FIG. 2.

FIGS. 2 and 3 show two schematic views of another embodiment of a photonic sensor chip 200 that includes a microfluidic substrate 210. The following description will refer to both figures in parallel. The photonic sensor chip 200 of the present embodiment comprises a photonic sensor core 220, which in the present example is a photonic sensor chip 100 as shown and explained in the context of the description of FIG. 1. A microfluidic substrate 210 is attached to the photonic sensor core 220 on the back side 216 of its semiconductor substrate 212. The microfluidic substrate 210 comprises a microfluidic channel 230, which in the present example connects an inlet 240 for a fluid and an outlet 250 for the fluid with the cavity 218. Since the back of the photonic sensor core 220 is formed by a planar silicon surface, the integration of microfluidics is considerably simplified compared to frontal integration.

The connection of the microfluidic substrate 210 to the semiconductor substrate 212 can be realized by wafer bonding for many of the materials mentioned. The ability to use a wafer bonding technique thus forms an additional advantage of the of the structure of the photonic sensor chip 200 which substantially simplifies the fabrication process.

The integration of microfluidic system 210 on the back side 216 of the semiconductor substrate 212 allows at least one fluid or gas to contact the active surface of the active-surface element 222 for allowing a detection of particles contained in the fluid or gas. Further, the use of microfluidics can increase the sensitivity of the measurement.

A biosensor resulting from this design can implement a laboratory diagnostic procedure integrated on a chip (lab-on-a-chip) and, in contrast to conventional on-site diagnostic procedures, is characterized by its miniaturization, sensitivity, parallelization and diversification possibilities. The advantage of the photonic measurement method proposed here over other label-free technologies that have already been developed is, on the one hand, the high inherent sensitivity of the measurement principle, the independence of the measurement signal from the amount of bound water and the possibility of producing cost-effective disposable chips. This approach combines the advantages of optical sensor technology (as with SPR) with the possibilities of chip production (as with SAW). In this way, components are provided that are suitable for practical use in bioanalytics.

Figure 4:
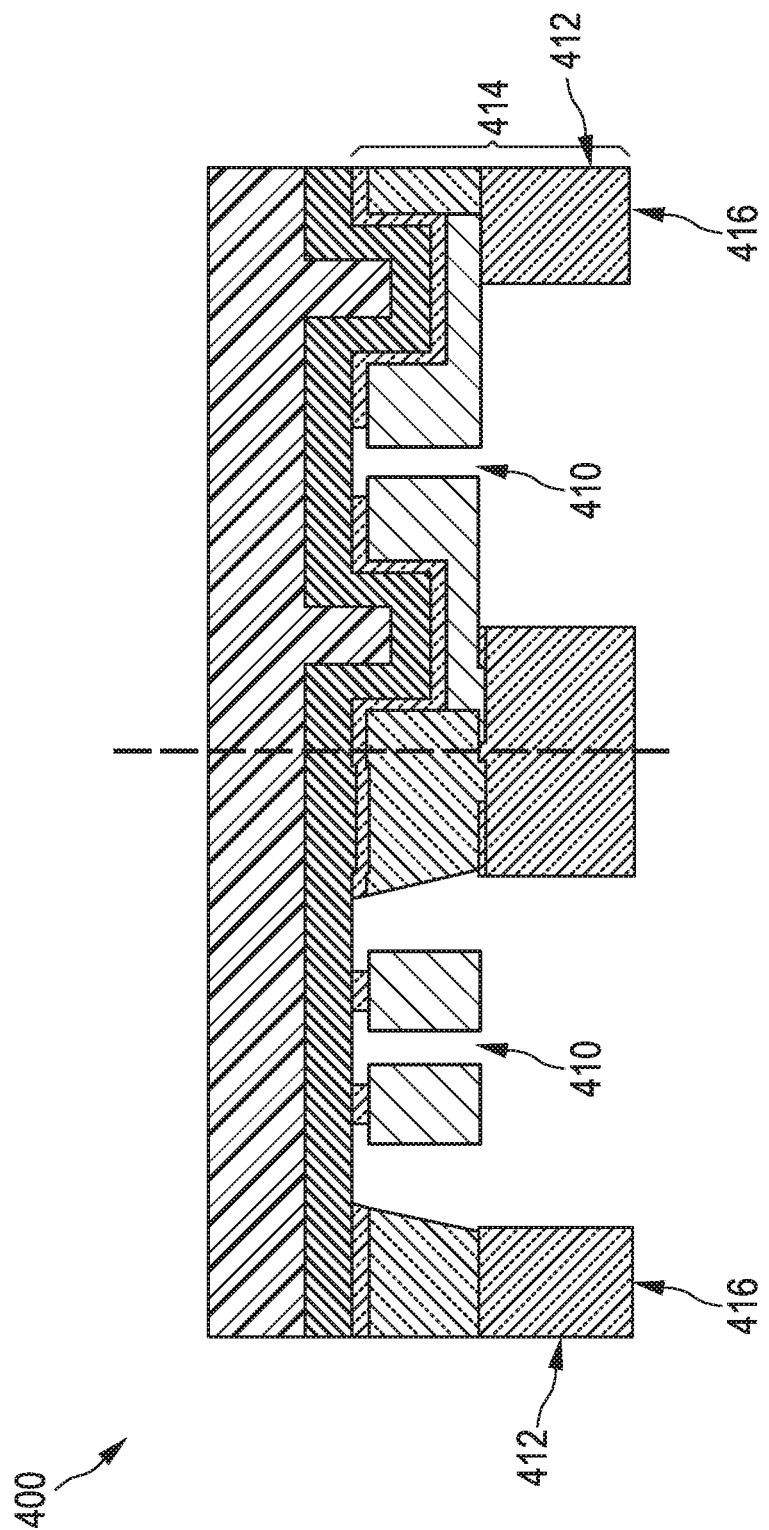
FIG. 4 shows a schematic cross-sectional view of different embodiments having different waveguide types, as used in embodiments of the photonic sensor chip.

As mentioned different waveguide types can be used in different embodiments of a photonic sensor chip. FIG. 4 shows a schematic cross-sectional view of different embodiments having different waveguide types 400, as used in embodiments of the photonic sensor chip. Two different types of slot waveguides 410 are presented in FIG. 4. Both types of the slot waveguide 410 are fabricated from the back side 416 of the semiconductor substrate 412 of a photonic sensor chip. Both slot waveguide 400s are located on an island-like silicon-on-insulator (SOI) structure 414.

Figure 5:
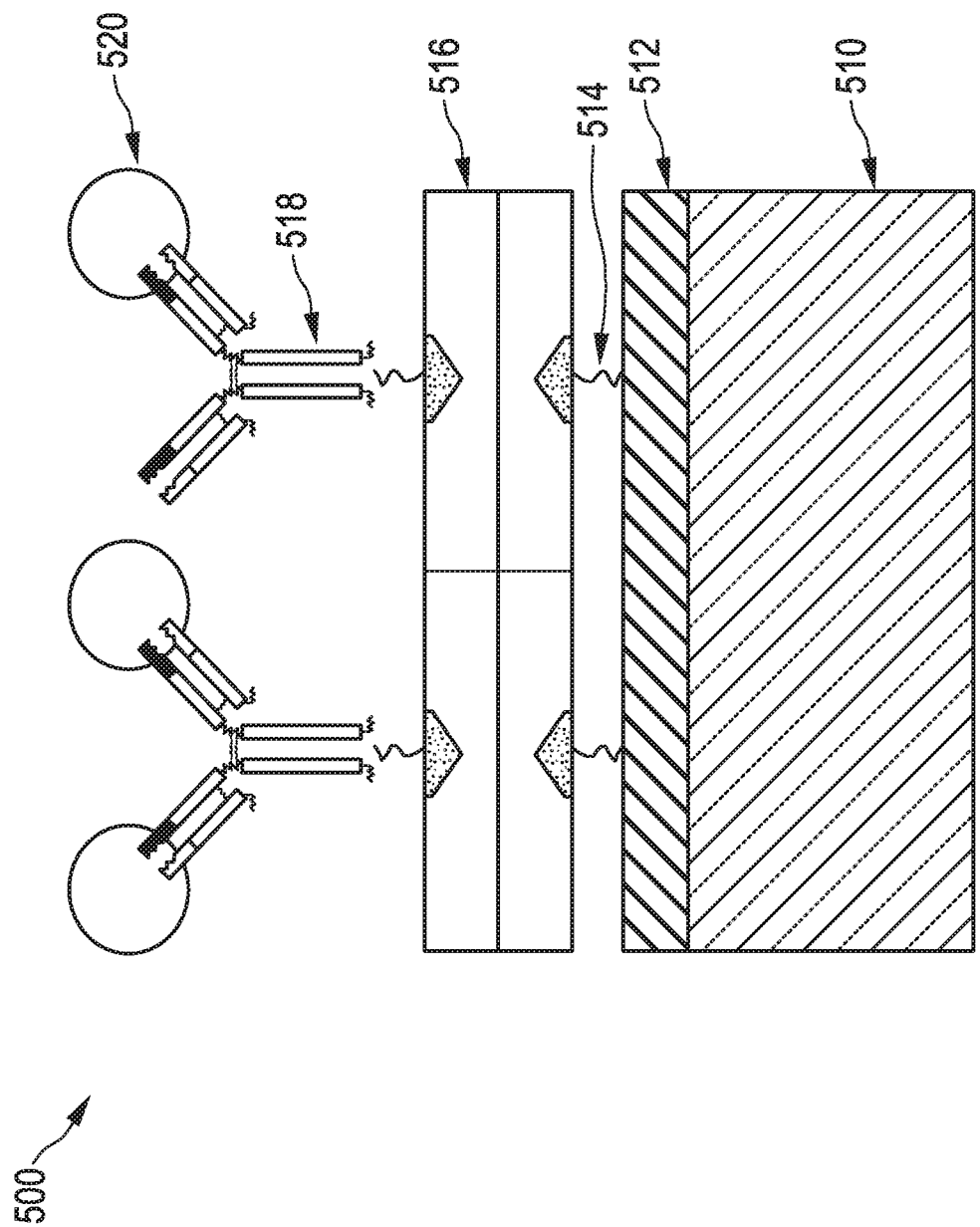
FIG. 5 shows a functionalized silicon waveguide section for specific application using a photonic sensor chip.

FIG. 5 shows a functionalized silicon waveguide section 500 for specific application using a photonic sensor chip. The waveguide 510 in this embodiment is made of silicon. Silicon can be functionalized with organosilanes, which have an organic group at one end. In this embodiment amino-propyl-triethoxisilane (APTES) 512 is used to chemically react in a silanization with the silicon waveguide 510. APTES has an amino-group at the end, which is not bonded to the silicon waveguide 510. The amino-group is covalently bonding biotin 514. Streptavidin molecules, which have a high affinity for biotin 514, are bonding to the biotin 514. Thus, a streptavidin 516 layer is formed. The streptavidin layer 516 can bind a biotinylated anti-CRP-complex 518, such that the waveguide section 500 has a functionalized surface section, which is suitable for specific detection of CRP molecules 520. Depending on the specification of the photonic sensor chip, other anti-complexes can be bonded.

Figure 6:
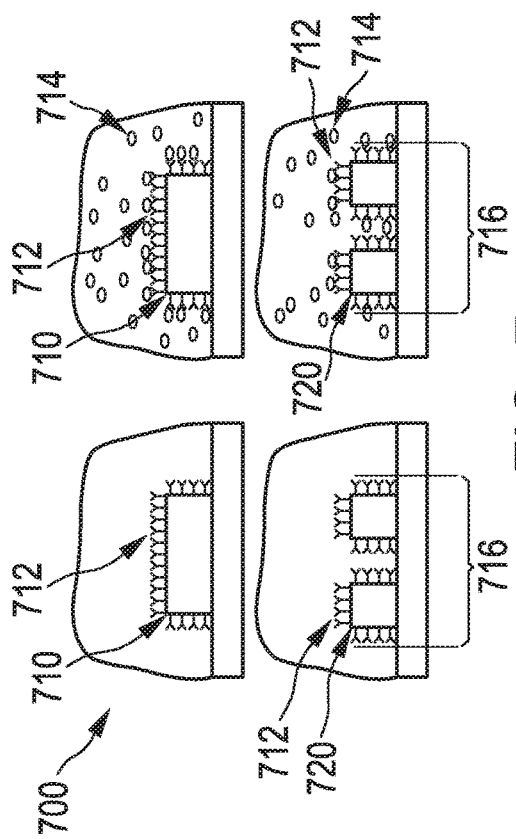
FIG. 6 shows illustrations of two different optical ring resonators for use in a photonic sensor chip.

Examples of biosensor designs are photonic devices that allow the conversion of a refractive index change into an evaluable signal. Examples of such transducer components are Mach-Zehnder interferometers, ring resonators and Fabry-Perot resonators. FIG. 6 shows illustrations of two different optical ring resonators 600 for use in a photonic sensor chip. Both ring resonator geometries form hybrid waveguide ring resonators. The ring resonators comprise a channel waveguide 610, such as in the upper example, or a slot waveguide 620, cf. the lower example. The detection limit for ring resonators is currently $10^{-5}$ RIU (refractive index unit). In order to realize a selective interaction of the optical input wave 630 with the active-surface element 640, the waveguide section 650 of the active-surface element is functionalized with specific ligands, as described above. Chip-integrated photonic sensors, such as optical ring resonators 600 can contribute to major advances in food diagnostics, environmental monitoring, veterinary diagnostics and medical technology through rapid and accurate analysis of a wide range of substances and offer the prospect of cost-effective on-site analysis.

Figure 7:
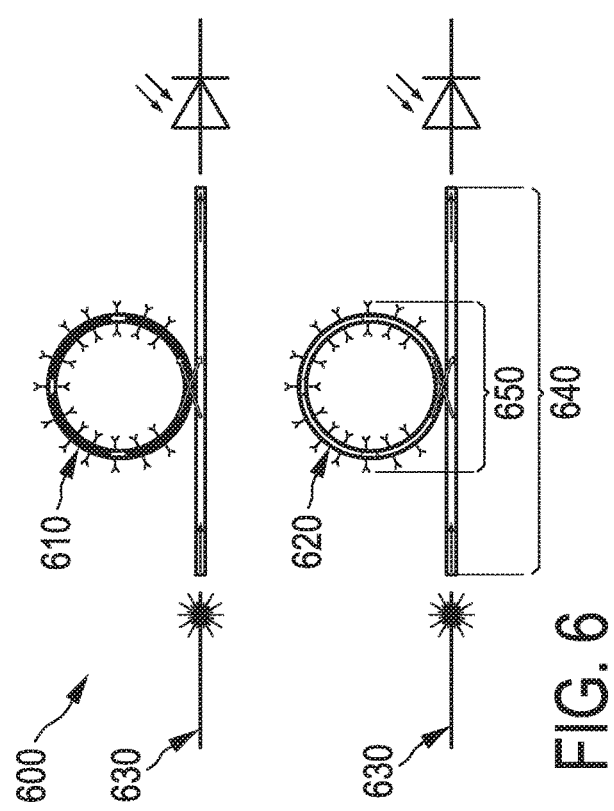
FIG. 7 shows a diagram of functionalized surface sections of different waveguides capturing particles using in a photonic sensor chip.

FIG. 7 shows a diagram of functionalized surface sections of different waveguides 700 capturing particles using in a photonic sensor chip. The upper left diagram shows a channel waveguide 710 arranged on the active-surface element, which has a functionalized surface section 716 functionalized with specific ligands 712. The functionalized surface 716 section is exposed to a fluid or gas without selected particles to be captured. The upper right diagram shows the mentioned channel waveguide 710 exposed to a fluid or gas with selected particles 714 to be captured. The selected particles 714 were captured by the specific ligands 712. The same principle works for a slot waveguide 720, which is shown in the lower row.

Figure 8:
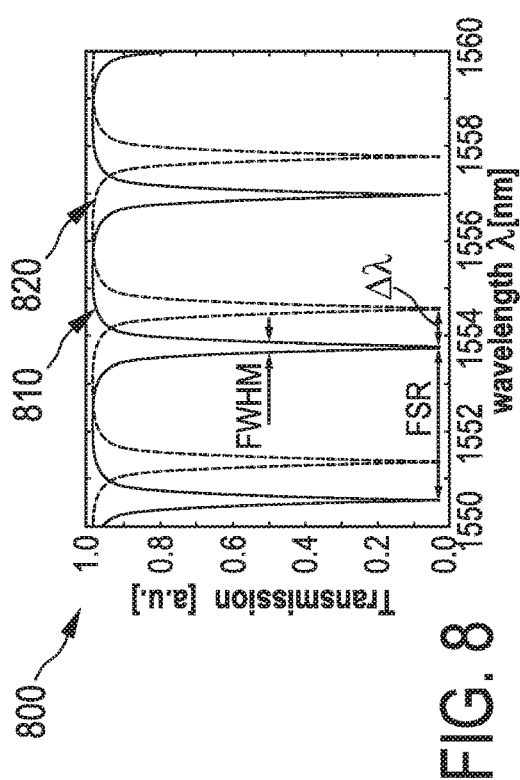
FIG. 8 shows transmission spectrum of measurement of the situations shown in FIG. 7 with a photonic sensor chip.

Label-free detection of biomolecules is thus enabled by integrating a photonic resonator or interferometer structure into the chip along with other photonic and electronic components. In order to realize a selective interaction with the analyte, the silicon-based waveguide 710, 720 of the photonic device is functionalized with specific antibodies. When the analyte interacts with the antibody, the propagation of the light wave is influenced, the resonance condition changes and the resonance wavelength is shifted. The magnitude of the wavelength shift provides information about the amount of adsorbed analytes and thus about its concentration in the solution to be analysed. FIG. 8 shows transmission spectrum 800 of measurement of the situations shown in FIG. 7 with a photonic sensor chip. The black line 810 in FIG. 8 represents a resulting optical output wave from the active-surface element to a light detector, which is not influenced by captured specific particles. When the specific particles captured by the specific ligands 712 the optical input wave is influenced. The resonance condition changes and the resonance wavelength is shifted by $\Delta\lambda$ (shown as red line in FIG. 8) resulting in a resulting optical output wave 820 from the active-surface element to a light detector, which is shifted by $\Delta\lambda$. The magnitude of the wavelength shift provides information about the amount of captured specific particles and thus about its concentration in the solution to be analysed.

With an ordinary silicon channel waveguide, the optical input wave is guided in the silicon waveguide and interacts only through an evanescent field with the captured specific particles. In comparison, silicon slit waveguides ensure a significantly increased interaction between the guided optical input wave and the captured specific particle, as a large part of the optical input wave up to 75% is guided in the slit and in the vicinity of the silicon webs where the captured specific particle is located. Thus, slot waveguides show a 3.5-fold greater light-particle interaction compared to channel waveguides.

FIG. 9 shows an embodiment of a photonic sensor arrangement 900. The photonic sensor arrangement comprises a packaged photonic sensor device 910 and a light source for generating the optical input wave, and an optical coupling element 914 for coupling the optical input wave into the photonic plane of the photonic sensor chip 916. The packaged photonic sensor device can generally be packaged using state of the art solutions, and includes a hole for providing access to the active-surface element of the particle sensor element of the photonic sensor chip a usage of the inventive photonic sensor chip cost-effective. The packaged photonic sensor device can be used as disposable product. In this embodiment, the light source and the optical element are arranged inside a housing 918. The optical input wave is coupled into the photonic plane of the photonic sensor chip, for instance, by an optical fiber. The housing 918 also includes a data transmission unit configured to receive the output signal from the data acquisition unit and to transmit the output signal to an external device an interface unit configured to receive the output signal from the data acquisition unit and to indicate an amount of particles captured by the active surface. Such photonic sensor arrangement 900 has the advantage that it is portable, which is of particular importance for the practical implementation.

The photonic biosensor allows the selective and label-free detection of proteins or substances in general for which a specific capture molecule exists. Such evidence is relevant in many areas. Examples are the detection of proteins in food, toxins in the environment as well as the detection of substances in various body fluids in medical diagnostics or therapy monitoring. In addition, the sensor can also be used as a sensor without functionalizing the silicon surface. For example, it can be used as a gas sensor in which a change in refractive index is measured. An application for temperature measurement is also conceivable.

Figure 10:
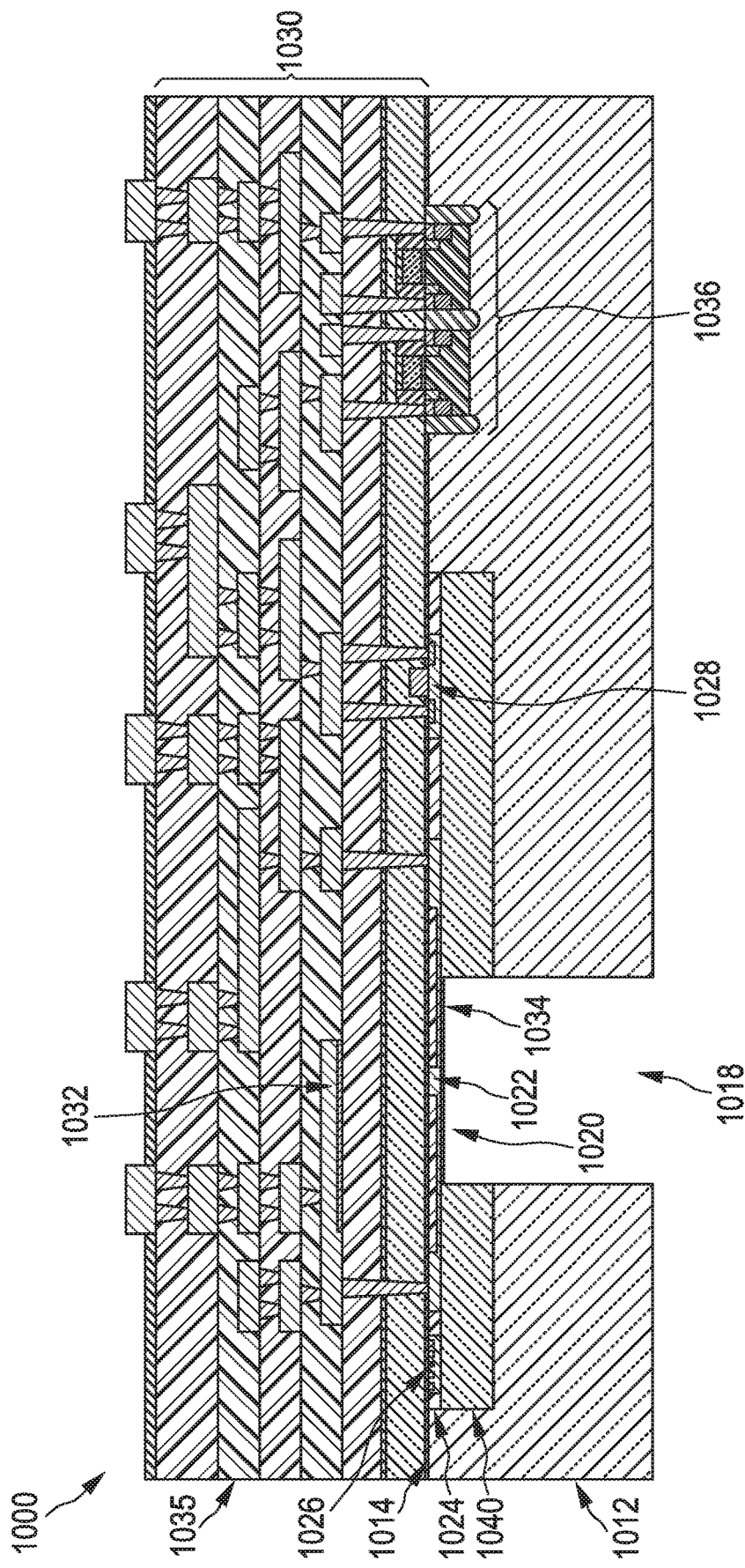
FIG. 10 shows a schematic cross-sectional view of an embodiment of a photonic sensor chip.

FIG. 10 shows a schematic cross-sectional view of an embodiment of a photonic sensor chip 1000. The photonic sensor chip 1000 has a semiconductor substrate 1012 having a front side 1014 and a back side 1016. The photonic sensor chip 1000 includes a cavity 1018 extending from the back side 1016 through an entire depth of the semiconductor substrate 1012, which is for example a silicon substrate. The cavity 1018 provides access to the active surface of the photonic particle sensor element 1020 from the back side 1016 of the semiconductor substrate 1012. A photonic particle sensor element 1020 is arranged on the front side 1014 of the semiconductor substrate 1012 in a photonic plane 1024. The photonic particle sensor element 1020 comprises an active-surface element 1022 for capturing particles that is exposed for access from the back side 1016 of the semiconductor substrate 1012. In this embodiment, the active-surface element 1022 comprises a waveguide section 1034 of a waveguide. An optical input wave is coupled into the photonic plane 1024 using a grating coupler 1026 arranged in the photonic plane 1024. The waveguide serves for guiding the optical input wave to the active-surface element, and further for guiding a resulting optical output wave to a light detector 1028, which in the present embodiment is a Ge-photodiode and is also arranged in the photonic plane 1024.

On the front side 1014 of the semiconductor substrate 1012 of the photonic sensor chip 1000, electronic components 1030 are arranged, which are fabricated using known front-end-of-line (FEOL) and the interconnect stack can be fabricated using standard back-end-of-line (BEOL) technologies. In this example, the FEOL fabrication involves manufacturing NMOS devices, PMOS devices and SiGe:C HBTs. The FEOL fabrication also involves manufacturing of the Ge-photodiode. The electronic components can for instance form a circuit section or a complete circuit of a control unit, a data acquisition unit or other electrical circuitry. The photonic sensor chip 1000 is thus a SiGe BiCMOS device 1036. A thermal heating element 1032 is arranged in a metal layer of an interconnect stack 1035 located above the functionalized surface section of the active-surface element. Locating the thermal heating element 1032 above the functionalized surface section of the active-surface element allows calibrating the resonance condition of the photonic particle sensor element 1020 and stabilizing the temperature during measurements at the same time. For calibration the optical resonance of the photonic particle sensor element is shifted such that, the optical input wave received by the photonic particle sensor element lies on the resonance flank or the resonance peak. Stabilization of the temperature during the measurement is essential due to very specific binding affinities of biomolecules, which shall be captured by the photonic particle sensor element 1020. The electrical interconnect stack 1035 comprises electrical interconnects 1038 for conducting electrical operating power to the mentioned electro-optical and electronic components and to conduct electronic signals to and from the electro-optical and electronic components to their respective destinations on chip or to an interface to external circuits. In this embodiment, the waveguide in the photonic plane 1024 is arranged on a local island-like silicon-on-insulator (SOI) structure 1040 that is embedded in the bulk of the silicon substrate 1012. The SiGe BiCMOS 1036 is located next to the local island SOI 1040 on the bulk of silicon substrate 1012.

Figure 11:
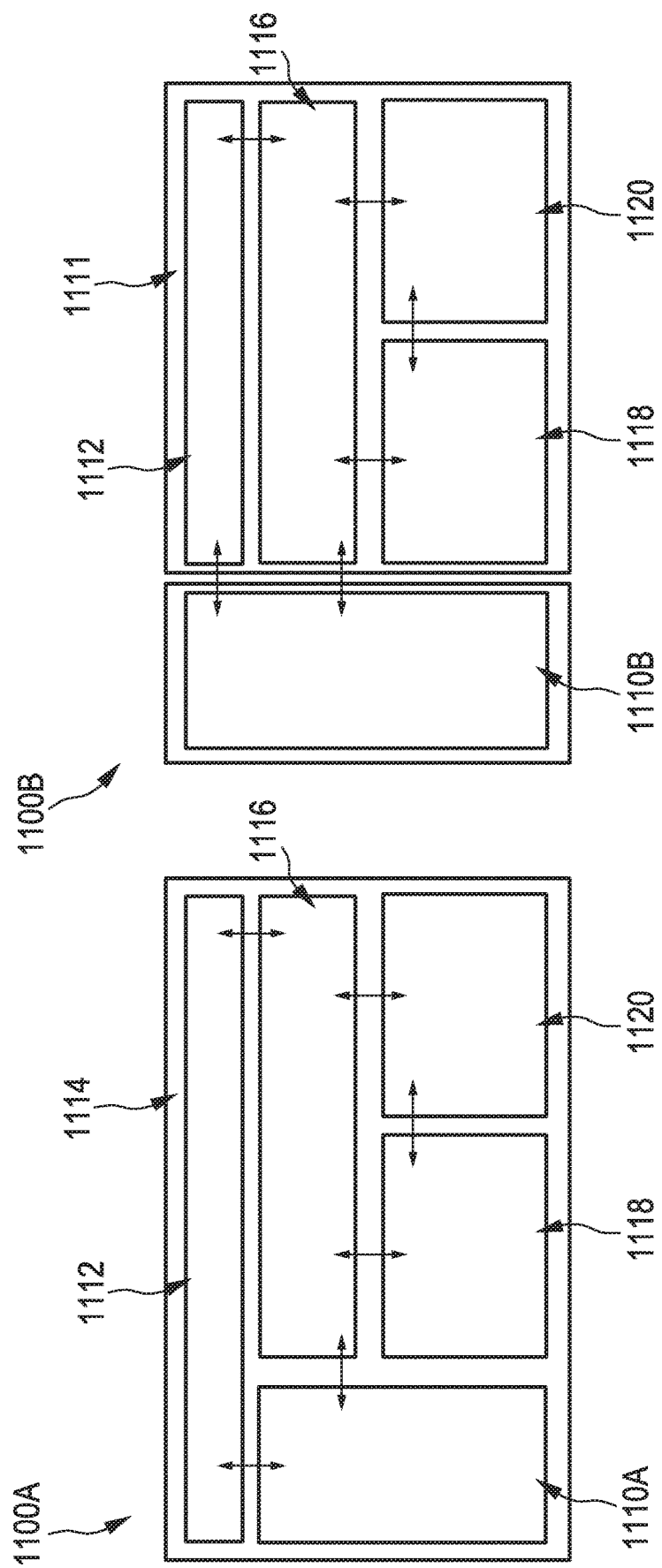
FIG. 11a shows a block diagram an embodiment of a packaged photonic sensor device.
FIG. 11b shows a block diagram another embodiment of a packaged photonic sensor device.

FIG. 11*a* shows a block diagram an embodiment of a packaged photonic sensor device 1100A. In this exemplary embodiment, the packaged photonic sensor device 1100A comprises a photonic sensor chip 1110A and an electronic control chip arranged on a carrier 1114. The electronic control chip electrically connected to the photonic sensor chip 1110A. The photonic sensor chip 1110A of the present embodiment is a photonic sensor chip 1110A as shown and explained in the context of the description of FIG. 1. The electronic control chip comprises a control unit 1112, which is configured to drive operation of the at least one photonic particle sensor element on the photonic sensor chip, and a data acquisition unit 1116, which is configured to sample an output signal of the light detector. Further, a data transmission unit 1118 configured to receive the output signal from the data acquisition unit and an interface unit 1120 configured to receive the output signal from the data acquisition unit 1116 and to indicate an amount of particles captured by the active surface are arranged in the electronic control chip.

For packaging, state of the art solutions can be used, including fabrication of a hole for providing access to the active-surface element of the particle sensor element of the photonic sensor chip 1110A.

FIG. 11*b* shows a block diagram another embodiment of a packaged photonic sensor device 1100B. In this embodiment, a photonic sensor chip 1110B and an electronic control chip 1111 are separately provided in separate chips, which may be individually packaged or provided in a system-on-chip and provided together in one package. For further details regarding the functionality of the photonic sensor chip 1110B and of the electronic control chip 1111 of this embodiment, reference is made to the description of FIG. 11*a*.

Figure 12:
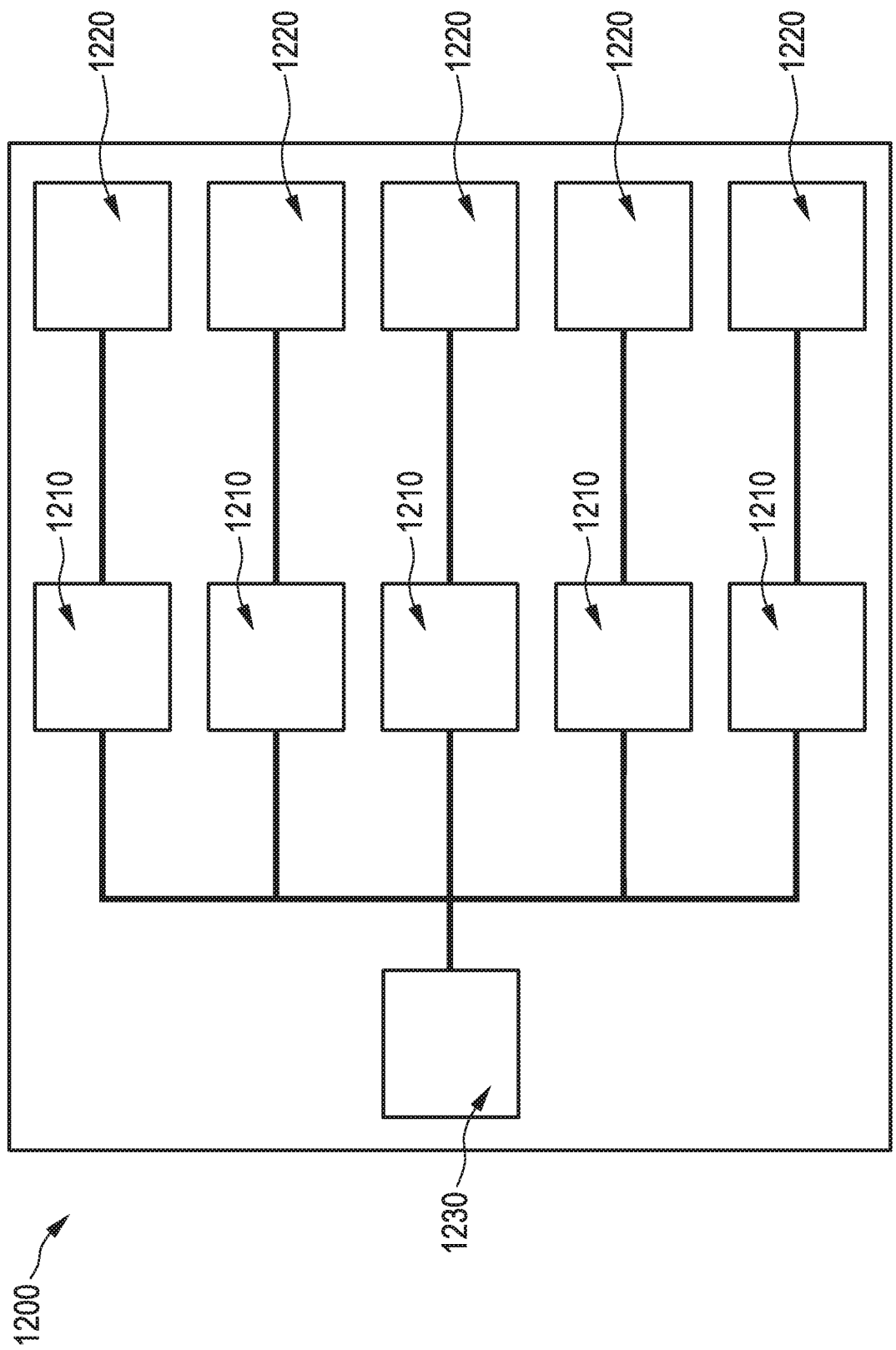
FIGS. 12 to 14 show block diagrams of different embodiments of the photonic sensor chip.
Figure 13:
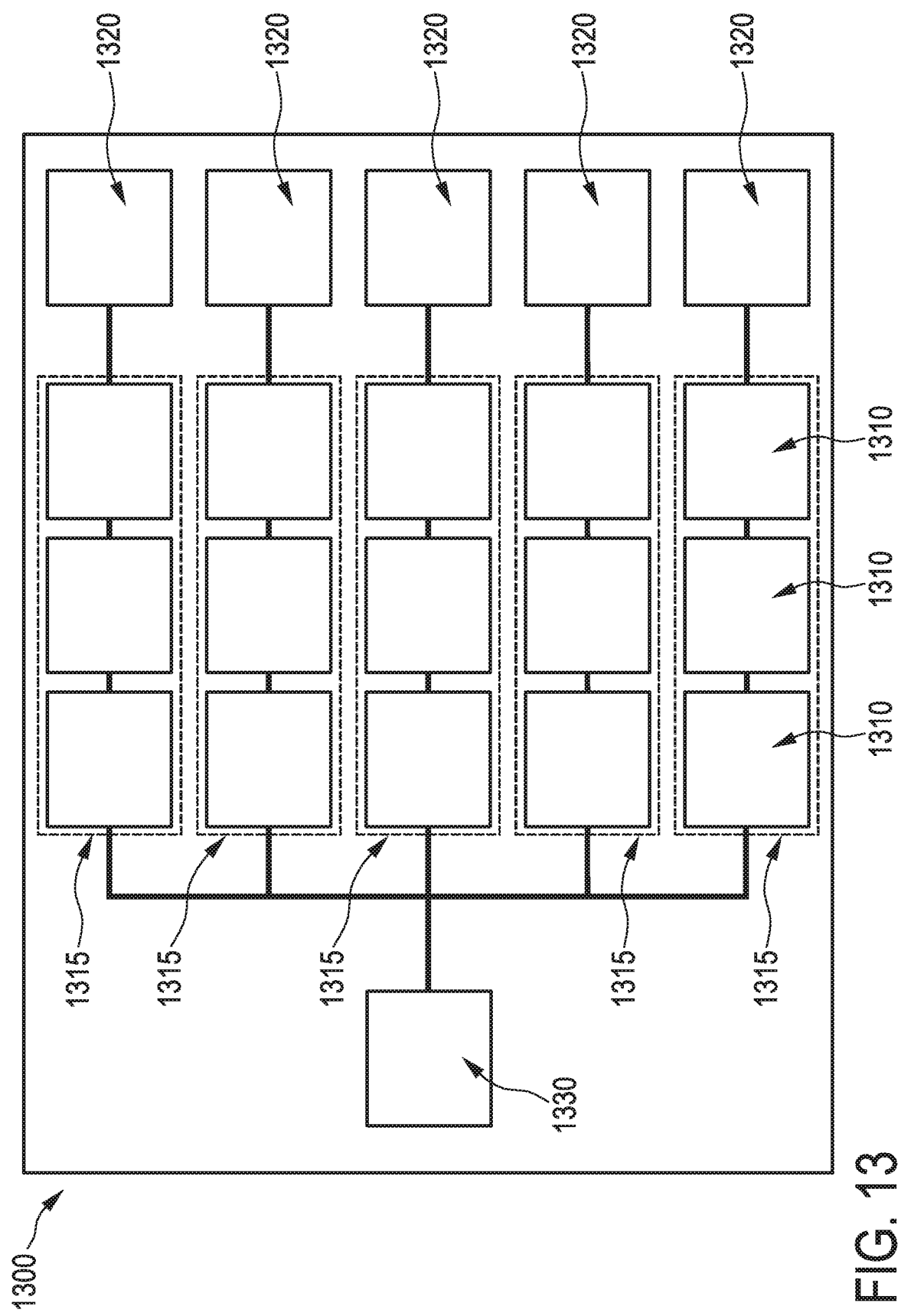
Figure 14:
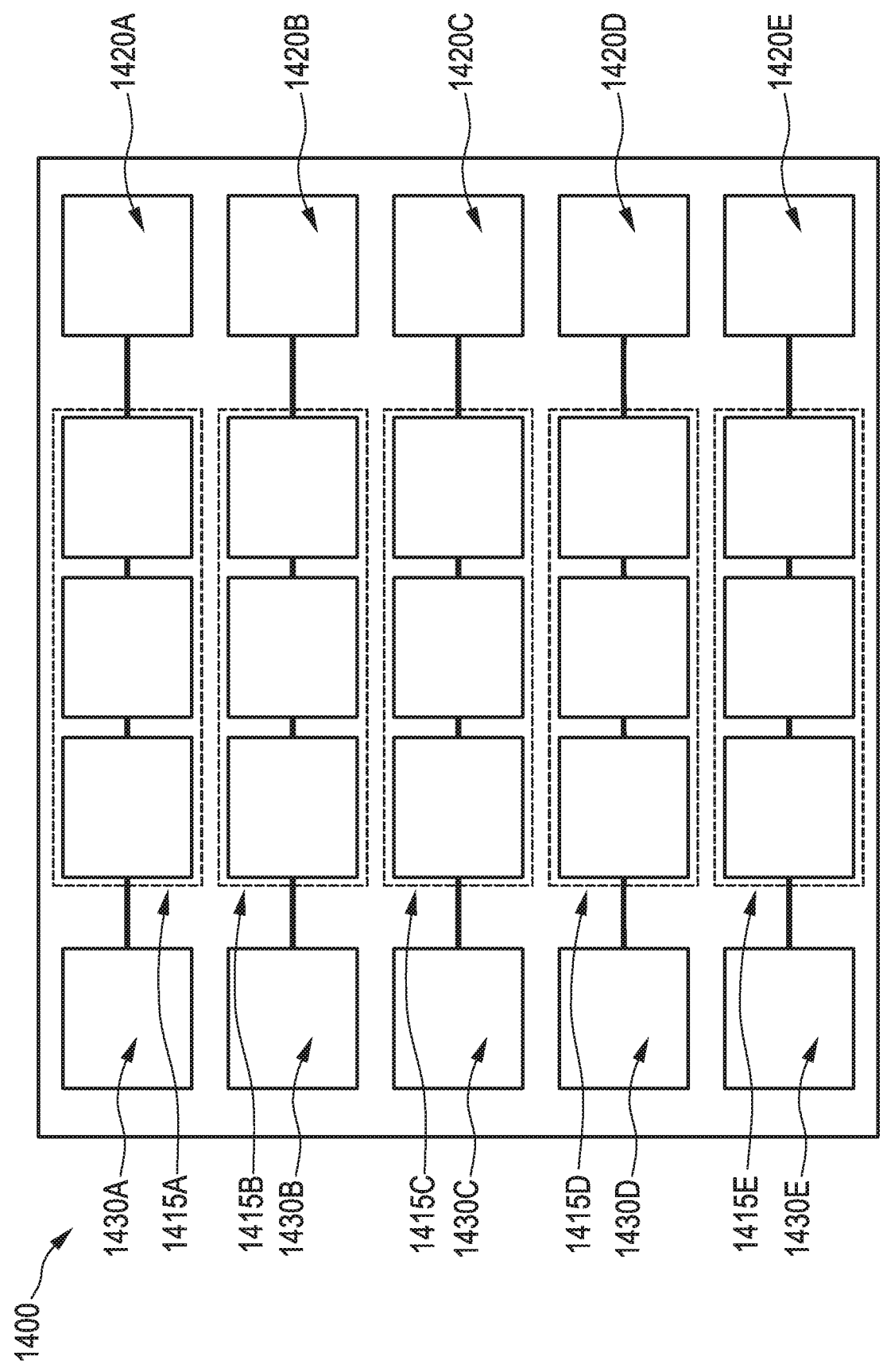

FIGS. 12 to 14 show different possibilities to arrange a plurality of active-surface elements in the photonic sensor chip.

FIG. 12 shows a possibility to arrange five active-surface elements in parallel 1200. Each active-surface element 1210 is arranged upstream of a photodiode 1220, which is used as light detector. One laser 1230 is used as light source for all active-surface elements 1210. An optical input wave transmitted by the laser can be splited to respective active-surface elements 1210. Such a parallel arrangement enables the detection of different selected particles in parallel.

The signal-to-noise ratio of an optical output wave to be transformed into a corresponding electrical signal received by the light detector, can be increased by using a series connection of active-surface elements. FIG. 13 shows a possible arrangement to derive benefit of a parallel arrangement 1300 of the active-surface elements 1310 and a series connection of active-surface elements 1315. In contrast to the arrangement in FIG. 12 three active-surface elements in series connection are arranged upstream of respective photodiodes 1320. The arrangement of laser 1330 and photodiodes 1320 remains the same as in FIG. 12.

FIG. 14 displays an exemplarily arrangement 1400, where five lasers 1430A to 1430E and five photodiodes 1420A to 1420E are arranged in parallel. In between, three identical active-surface elements 1415A to 1415E are optically arranged in a series connection. Such arrangement of active-surface elements 1415A to 1415E allows to increase the signal-to-noise ratio of the resulting optical output wave to be transformed into a corresponding electrical signal by the photodiode due to the series connection. This arrangement 1400 also enables to detect of different selected particles in parallel due to the parallel connection.

As an application example of the photonic sensor chip, allergens in food (such as peanuts) or toxins (e.g. snake venom, toxic insects, scorpions, spiders, blue-green algae, mould poisons or poisonous fungi) can be investigated. Further applications of the photonic sensor chip are listed Table 1 below and can be followed or applied on the basis of the results obtained. The left column of the following table lists different analytes, and the right column list possible occurrences of the respective analytes.

TABLE 1

Application cases of the photonic sensor chip

| analyte | Occurrence |
| --- | --- |
| toxins | |
| aflatoxins | nuts, corn, milk |
| ergot alkaloids | cereals |
| fusarium toxins | cereals, maize |
| patulin | Apples, pears |
| ochratoxin | Cereals, beer, wine, coffee, nuts, spices |
| bacteria | |
| *Salmonella* (zoonoses) | eggs, poultry, water |
| *Escherichia coli* | raw milk, vegetables, water, minced beef, sprouts |
| campylobacter | Raw poultry meat |
| *shigella* toxin | food |
| viruses | |
| Influenza A virus H1N1 | birds, pig |
| allergens | |
| gluten | food |
| antibiotics | |
| penicillins | Waste water Meat Milk |
| hormones | Water |

An important application potential is currently seen in the detection of contaminations such as antibiotics in raw milk.

A cow is milked at least twice a day. The fresh raw milk is automatically piped into the cooling tank of the production plant. In principle, the raw milk is collected every one to two days from the producer in the milk collection truck. Depending on the vehicle type, this can hold between 10,000 and 25,000 litres. Once the smell, colour and temperature of the raw milk have been checked, it is pumped from the cooling tank into the milk collection truck. Milk samples are automatically taken and analysed in an independent laboratory or in the dairy. Once it arrives at the dairy, the raw milk is subjected to microbiological and chemical-physical checks for cleanliness, smell, taste, appearance, purity, fat content, acidity, germ content and weight. The milk is then pumped into large storage tanks. Seamless quality assurance from the producer to the refrigerated shelf is a matter of course for the German dairy industry. In order to further improve product safety, many dairies are developing additional quality assurance systems that go beyond the legal requirements. The close cooperation of all stakeholders within the value chain is crucial to ensure the production of safe and high quality products. The developed hybrid waveguide ring resonator can make a major contribution to this. In addition to fast on-site analysis, the sensor also enables digital evaluation and creation of databases without intermediate steps.

In summary, the solution proposed here considerably simplifies the development of a connection technique and the handling of the sensor, since the sensor surface is separated from the electronics and the light injection. This allows an analyte to interact with the sensor from the rear and does not interfere with further chip build-up. It is thus possible to manufacture the chip from the front with all the usual process steps, which also allows monolithic integration of the sensor. In monolithic integration, the photonic sensor is manufactured together with optoelectronic components (e.g. photodiodes) and electronic components (e.g. heating element). The bioanalytic part is accessible through the rear opening in the form of a cavity connecting to the optical sensor. For this purpose, a wafer, on which the photonic components are located, is etched from the reverse side in such a way that the areas with the sensor surfaces are exposed and can be functionalized with antibodies.

This also allows the integration of microfluidics on the back of the chip. Since the back of the chip consists of a planar silicon surface, the integration of microfluidics is considerably simplified compared to frontal integration.

The solution proposed has the following advantages:

Decentralized diagnostics without laboratory diagnostic prior knowledge

A mobile sensor platform enables fast on-site diagnostics

Measurement of several biological substances and parameters in parallel and in short time can be enabled Functionalized surfaces with customized properties for bioanalytics The optical biosensor can be used for almost any requirements in medicine and industry due to its adaptable and functional optical waveguides Compatibility of photonic with electronic components on one chip without additional process steps (integration with separation of electrical and biosensory environment)

Low-cost in terms of manufacturing and disposal costs (due to the CMOS technology used and the avoidance of complex and very expensive flow cells)

Suitable for mass production, as the manufacturing and process technology is designed at wafer level Low power requirements and extremely high compactness (this offers the possibility of sensor arrays on a small area and the realization of mobile, battery-powered devices).

What is claimed is:

1. A packaged photonic sensor device, comprising:
 a photonic sensor chip comprising:
  a semiconductor substrate having a front side and a back side;
  at least one cavity extending from the back side through an entire depth of the semiconductor substrate;
  a photonic plane located on the front side of the semiconductor substrate and including at least one photonic particle sensor element with an active-surface element having an exposed active surface facing towards the back side of the semiconductor substrate and configured for capturing selected particles from at least one fluid or gas to which the active surface is exposable, wherein the least one cavity provides access to the active surface from the back side of the semiconductor substrate; and wherein the photonic particle sensor element is configured to receive an optical input wave via the photonic plane, to expose particles captured by the active-surface element to interact with the optical input wave and to provide a resulting optical output wave having a spectral component indicative of the interaction between the optical input wave and the captured particles; and a waveguide arranged in the photonic plane for guiding the optical input wave to the active-surface element and for guiding the resulting optical output wave from the active-surface element to a light detector of the photonic particle sensor element, which is configured to generate an output signal in response to receiving the optical output wave; the photonic sensor chip further comprising an electrically drivable phase shifter element, which is configured to set and maintain a predetermined phase shift to be effected by the active-surface element alone, and an electronic control chip electrically connected to the photonic sensor chip arranged on a carrier and comprising a control unit, which is configured to drive operation of the at least one photonic particle sensor element on the photonic sensor chip and a data acquisition unit configured to sample an output signal of the light detector; and a package enclosing the photonic sensor chip and the electronic control chip and having an opening to ambient atmosphere facing the back side of the semiconductor substrate of the photonic sensor chip for providing access to the exposed active surface of the at least one photonic particle sensor element for the at least one fluid.

2. The packaged photonic sensor device according to claim 1, wherein the photonic sensor chip further comprises:
a control unit, which receives the output signal of the light detector and is configured to drive operation of the at least one photonic particle sensor element; wherein
the control unit is configured to drive operation of the phase shifter element in dependence on the received output signal of the light detector in order to set and maintain a predetermined phase shift to be effected by the active-surface element alone.

3. The packaged photonic sensor device according to claim 1, wherein the electrically drivable phase shifter element comprises an electrically drivable heating element embedded in the electrical interconnect stack, or an electrically drivable doped waveguide.

4. The packaged photonic sensor device according to claim 2, wherein the photonic sensor chip further comprises
a data acquisition unit configured to sample an output signal of the light detector; and
an electrical interconnect stack, which is arranged on top of the photonic plane and comprises electrical interconnects for conducting electrical operating power and to conduct electronic signals to and from the control unit and the data acquisition unit.

5. The packaged photonic sensor device according to claim 1, wherein a microfluidic substrate is connected to the back side of the semiconductor substrate and comprises at least one microfluidic channel connecting an inlet for the fluid and an outlet for the fluid with the cavity.

6. The packaged photonic sensor device according to claim 5, wherein the microfluidic substrate is made of a plastic, glass or semiconductor.

7. The packaged photonic sensor device according to claim 1, wherein the active-surface element comprises a waveguide section of the waveguide, wherein the waveguide section
comprises at least one functionalized surface section configured for capturing the selected particles by selective interaction, and
has an optical path length that depends on an amount of particles captured by the active surface.

8. The packaged photonic sensor device according to claim 7, wherein the photonic particle sensor element comprises a plurality of active-surface elements optically arranged in a series connection and upstream of the light detector.

9. The packaged photonic sensor device according to claim 7, wherein the functionalized surface section is functionalized chemically.

10. The packaged photonic sensor device according to claim 7, wherein the functionalized surface section is functionalized physically.

11. The packaged photonic sensor device according to claim 1, wherein the waveguide is substantially made of silicon, silicon nitride, silicon oxynitride or germanium.

12. The packaged photonic sensor device according to claim 1, wherein the photonic sensor chip further comprises
at least one light source connected to the waveguide and configured to generate and emit the optical input wave.

13. A photonic sensor arrangement, comprising:
a packaged photonic sensor device according to claimer 1, and
a light source for generating the optical input wave, and an optical coupling element for coupling the optical input wave into the photonic plane of the photonic sensor chip.

14. The photonic sensor arrangement of claim 13, further comprising on the carrier
a data transmission unit configured to receive the output signal from the data acquisition unit and to transmit the output signal to an external device; and
an interface unit configured to receive the output signal from the data acquisition unit and to indicate an amount of particles captured by the active surface.

* * * * *